(12) United States Patent
Kobayashi et al.

(10) Patent No.: US 9,638,677 B2
(45) Date of Patent: May 2, 2017

(54) CHROMATOGRAPH MASS SPECTROMETER

(71) Applicant: SHIMADZU CORPORATION, Kyoto-shi, Kyoto (JP)

(72) Inventors: Yuko Kobayashi, Kyoto (JP); Hiroshi Sugawara, Kyoto (JP); Tairo Ogura, Columbia, MD (US)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/914,354

(22) PCT Filed: Aug. 26, 2013

(86) PCT No.: PCT/JP2013/072702
§ 371 (c)(1),
(2) Date: Feb. 25, 2016

(87) PCT Pub. No.: WO2015/029101
PCT Pub. Date: Mar. 5, 2015

(65) Prior Publication Data
US 2016/0209378 A1 Jul. 21, 2016

(51) Int. Cl.
*H01J 49/00* (2006.01)
*G01N 30/72* (2006.01)
(Continued)

(52) U.S. Cl.
CPC ......... *G01N 30/72* (2013.01); *G01N 30/8644* (2013.01); *H01J 49/0031* (2013.01); *H01J 49/4225* (2013.01)

(58) Field of Classification Search
None
See application file for complete search history.

(56) References Cited

U.S. PATENT DOCUMENTS

2015/0194296 A1* 7/2015 Verenchikov ....... H01J 49/0027
250/282

FOREIGN PATENT DOCUMENTS

JP 2011-141220 A 7/2011
JP 2011141220 A * 7/2011
(Continued)

OTHER PUBLICATIONS

Written Opinion for PCT/JP2013/072702 dated Nov. 26. 2013. [PCT/ISA/237].
(Continued)

*Primary Examiner* — Andrew Smyth
(74) *Attorney, Agent, or Firm* — Sughrue Mion, PLLC

(57) ABSTRACT

When setting analysis conditions, an analysis operator sets, on a dwell-time calculation/loop-time listing window, the target value of a loop time corresponding to the measurement-time interval to repeat an analysis for one ion, and clicks a dwell time calculation button. Then, a dwell time calculator computes the dwell time for each event, based on the target value of the loop time, the arrangement of events set at that point in time, the number of target ion species set in each event, and other conditional factors. The calculated result is displayed in a dwell time calculation result display field in a listing table. The largest and smallest values of the dwell time are displayed in the largest/smallest dwell time display field. The analysis operator checks this display and changes the target value of the loop time and/or the measurement time of the event so as to achieve an appropriate dwell time.

9 Claims, 9 Drawing Sheets

(51) Int. Cl.
    *G01N 30/86*     (2006.01)
    *H01J 49/42*     (2006.01)

(56) References Cited

FOREIGN PATENT DOCUMENTS

| JP | 2012-132799 A | | 7/2012 |
|---|---|---|---|
| JP | 2012132799 A | * | 7/2012 |

OTHER PUBLICATIONS

International Search Report for PCT/JP2013/072702, dated Nov. 26, 2013.
International Search Report for PCT/JP2013/ 072703, dated Nov. 26, 2013.

* cited by examiner

Fig. 7

| TYPE | EVENT# | +/- | COMPOUND NAME m/z |
|---|---|---|---|
| MRM | 1 | + | 193.00>122.00 |
| MRM | 2 | + | 100.00>100.00 |
| MRM | 3 | + | 100.00>100.00 |

MEASUREMENT TIME: 0 - 3 min

| Ch | PRECURSOR m/z | PRODUCT m/z | DWELL TIME (msec) | COLLISION ENERGY |
|---|---|---|---|---|
| Ch1 | 193.00 | 122.00 | 1.0 | -35.0 |
| Ch2 | | | | |
| Ch3 | | | | |
| Ch4 | | | | |
| Ch5 | | | | |

EVENT TIME: 0.004 sec

Q1 RESOLVING POWER: Unit
Q3 RESOLVING POWER: Unit

ADD POSITIVE   ADD NEGATIVE   END TIME 6.000 min

MRM(+)   PRODUCT ION SCAN(-)   PRECURSOR ION SCAN(-)   NEUTRAL LOSS SCAN(-)   SIM(+)   SCAN(-)

USE CID GAS   CID GAS

SHOW LOOP TIME

TIME (0.000 min – 5.000 min)

COMPOUND NAME:

Fig. 8

| LOOP TIME LIST | | | | | |
|---|---|---|---|---|---|
| START-END TIME(min) | 0.000- | 0.500- | 1.000- | 1.500- | 2.000-3.000 |
| NUMBER OF EVENTS | 1 | 2 | 3 | 2 | 1 |
| LOOP TIME(sec) | 0.103 | 0.206 | 1.206 | 1.103 | 0.103 |

LARGEST EVENT NUMBER: 3    LARGEST LOOP TIME(sec): 1.206

CLOSE

CHROMATOGRAPH MASS SPECTROMETER

CROSS REFERENCE TO RELATED APPLICATIONS

This application is a National Stage of International Application No. PCT/JP2013/072702 filed Aug. 26, 2013, the contents of all of which is incorporated herein by reference in its entirety.

TECHNICAL FIELD

The present invention relates to a chromatograph mass spectrometer which consists of a Chromatograph coupled with a mass analyzer, such as a gas chromatograph mass spectrometer or liquid chromatograph mass spectrometer. More specifically, it relates to a chromatograph mass spectrometer for performing, in the mass analyzer, a selected ion monitoring (SIM) measurement, multiple reaction monitoring (MRM) measurement (which may also be called the "selected reaction monitoring (SRM) measurement") or similar measurements on a known compound.

BACKGROUND ART

Chromatograph mass spectrometers which consist of the combination of a chromatograph, such as a gas chromatograph (GC) or liquid chromatograph (LC), and a mass analyzer, such as a quadrupole mass analyzer, have been widely used for qualitative and quantitative determinations of various components contained in a sample. In general, when the quantitative determination of a known compound is performed with a chromatograph mass spectrometer, an SIM measurement method for selectively and repeatedly detecting one or more ions having previously specified mass-to-charge ratios is used.

When the quantitative determination of a known compound is performed using a chromatograph mass spectrometer consisting of a chromatograph (e.g. GC or LC) coupled with a triple quadrupole mass analyzer, an MRM measurement method is used, in which an ion having a specific mass-to-charge ratio (precursor ion) is selected by a front quadrupole mass filter, this ion is then fragmented in a collision cell by a collision-induced dissociation process, an ion having a specific mass-to-charge ratio among the product ions produced by the fragmentation is selected by a rear quadrupole mass filter, and the selected ion is detected. The MRM measurement method is advantageous in that the influence of foreign substances can be removed by the two quadrupole mass filters, so that the S/N ratio of the detection signal is improved and a higher level of sensitivity is achieved in quantitative determinations.

Normally, when an SIM or MRM measurement is performed with a chromatograph mass spectrometer in this manner, the component to be detected is previously known and the required task is to detect that component with the highest possible level of sensitivity. To this end, the analysis operator must set appropriate analysis conditions so that the highest possible level of sensitivity of the analysis will be achieved. A procedure for setting the analysis conditions in a conventional and common type of chromatograph mass spectrometer is described using FIGS. 7-9C.

When an analysis operator performs a predetermined operation on a control computer, a method-editing window 500 as shown in FIG. 7 is displayed. In the present example, the method-editing window 500 has an event information table 501 in its upper area and a channel information table 502 in its lower area, the latter table allowing the setting of the conditions for SIM-measurement-type events. An "event" is a measurement to be performed under one analysis condition in a series of analyses. In the event information table 501, each row corresponds to one "event", while the columns in table 501 show various items of information related to each event, such as the event number, analysis mode (labelled as "TYPE"), ion polarity (labelled as "+/−"), mass-to-charge ratios of the ions to be monitored, and measurement time range. The "SIM-measurement type" is a type of measurement for selectively detecting an ion having a specific mass-to-charge ratio. Specifically, it includes the SIM measurement and the MRM measurement.

On the method-editing window 500, the analysis operator clicks one of the two radio buttons arranged in the polarity selection button area 503 to select the polarity of the ion to be analyzed in an event which is to be added. Subsequently, the analysis operator clicks one of the buttons arranged in the analysis mode addition button area 504 to select an analysis mode to be added (e.g. "MRM", "Precursor Scan", etc.). By such operations, an event for performing the selected analysis mode is added to the event information table 501. In the example of FIG. 7, three events have been set, with the MRM measurement selected as the analysis mode in all of them.

In the case where the analysis mode is the SIM-measurement type, or more specifically, in the case of an MRM or SIM measurement, a plurality of ions can be set in the channel information table 502 as the ions to be monitored in one event. Furthermore, in the case of the MRM measurement, the mass-to-charge ratio of the precursor ion and that of the product ion are individually set, as shown in FIG. 7. The two text boxes arranged in the measurement time input area 505 allows the setting of the measurement time range of the event by entering the measurement starting time and measurement finishing time. The measurement time range set in this area is graphically shown by a bar graph in the measurement-time display field 501a in the event information table 501 (see Patent Literature 1).

In general, analysis operators need to pay attention to the following points in setting the measurement time range of each event:

(1) The measurement time range should be set with a certain amount of extra time before and after the retention time of the target compound, since the point in time at which the compound is actually eluted from the column does not exactly coincide with its retention time.

(2) In the SIM-type measurement, the overlapping of a plurality of events should be avoided as much as possible in order to maximize the detection sensitivity. Naturally, in the case of a simultaneous multicomponent analysis, it is impossible to completely avoid the overlapping of the events. Accordingly, the overlapping of the events is allowed for a compound for which the problem of detection sensitivity is unlikely to occur (e.g. when the content of the compound is known to be high), whereas care should be taken to minimize the overlapping of the events for a compound for which the problem of detection sensitivity is likely to occur (e.g. when the content of the compound is known to be low).

After setting the events and appropriately adjusting the measurement time range of each event, when the analysis operator clicks a loop-time display button 506 in the method-editing window 500, a loop-time checking window 600 as shown in FIG. 8 is displayed. The relationship between the event time and the loop time is hereinafter described with reference to FIGS. 9A-9C.

FIGS. 9A-9C are model diagrams showing the relationship between the event time and the loop time in the case where a plurality of events are temporally overlapped. In this example, as shown in FIG. 9A, "Event 1(+)" (where "+" denotes a mode for detecting positive ions, while "−", which will be mentioned later, means a mode for detecting negative ions) includes four channels labelled as Ch1-Ch4 and sequentially detects four kinds of ions with different mass-to-charge ratios in a time-shared manner. In the case of a quadrupole mass analyzer, each of the ions with different mass-to-charge ratios is selected by switching the voltage applied to the quadrupole mass filter. Therefore, every time the channel is switched within one event, a "pause time" in which the collection of data is suspended is set. During this pause time, the applied voltage is switched and stabilized. After that, the period of time in which the detector actually receives and accumulates ions, i.e. the data-collecting time, is provided as the "dwell time."

In the present example, as shown in FIG. 9B, the four events, i.e. Event 1(+), Event 2(+), Event 3(−) and Event 4(−) are temporally overlapped. These four events are sequentially performed in a time-shared manner. The period of time required for one cycle of processes in which each of these four events is performed one time is the loop time. For example, in Ch1 of Event 1, in which a certain kind of ion species is detected, the detecting operation is performed in such a manner that the next detection of this ion species is performed after the loop time has elapsed since the previous detection of the same ion species. In other words, the interval of time of the detection of the same ion species is the loop time. As can be understood in FIG. 9C, when observing a peak on a chromatogram, using a longer loop time increases the interval of the neighboring data points, making it difficult to correctly grasp the peak shape. Therefore, particularly in the case of a quantitative analysis, it is important to reduce the loop time so that it does not exceed a certain value.

When an ion having a different polarity is to be detected, it is necessary to change the polarity of most of the voltages applied to the ion source, ion transport optical systems and other components in the mass analyzer. Therefore, as shown in FIG. 9B, when the polarity of the ion to be detected changes, a polarity-switching time is provided before the event time.

As shown in FIG. 8, an automatically calculated loop time is displayed in the loop-time listing table 601 arranged in the loop-time checking window 600. The automatic calculation of the loop time is disclosed in Patent Literatures 1 and 2 as well as other documents.

As can be understood from the foregoing explanations, the loop time normally depends on the number of overlapping events. Accordingly, the loop time is calculated for each range of time in which the number of overlapping events changes. In the largest loop-time display field 602 below the loop-time listing table 601, the value of the largest loop time within the entire measurement time is displayed. While visually checking the loop time in this window 600, the analysis operator appropriately adjusts the dwell time, event time, measurement time range and other parameters set in the method-editing window 500 so that the number of data points per one peak on the chromatogram will be an appropriate value.

As explained earlier, the dwell time is the period of time in which the acquisition of the data based on the ion intensity signal is actually performed. Accordingly, it considerably affects the detection sensitivity. Therefore, normally, a long dwell time is set when the detection sensitivity is low, while a short dwell time is set when the detection sensitivity is high. However, setting too short a dwell time lowers the level of the ion intensity signal and causes a decrease in the S/N ratio or worsens the peak shape on the chromatogram, which consequently decreases the accuracy of the peak area and possibly lowers the reliability of the quantitative determination. On the other hand, setting too long a dwell time causes a corresponding increase in the loop time, which also lowers the reliability of the quantitative determination due to various problems, such as the incorrect grasping of the peak top on the chromatogram or an incorrect approximation of the shape of the curve in the rising or falling phase of the peak. For these reasons, it is not always easy to appropriately set the dwell time; even an analysis operator with a certain amount of experience normally needs a considerable amount of time for this task.

CITATION LIST

Patent Literature

Patent Literature 1: JP 2011-141220 A
Patent Literature 2: JP 2012-13799 A

SUMMARY OF INVENTION

Technical Problem

The SIM-type measurement is frequently used for simultaneous multicomponent analyses for the residual pesticide testing, water examination or other purposes. Therefore, chromatograph mass spectrometers are designed to allow the setting of a large number of events. For example, a conventionally used control software application for a chromatograph mass spectrometer allows 512 events to be set in one method file. If such a large number of events need to be set, the task of setting an appropriate dwell time for each event while visually checking the loop-time checking window requires the analysis operator to consume an extremely high amount of time and labor. Furthermore, in the first place, the task is so complex that the setting of an appropriate dwell time for performing a sufficiently reliable quantitative determination is difficult.

The present invention has been developed to solve the previously described problem its primary objective is to provide a chromatograph mass spectrometer capable of reducing the amount of time and labor for an analysis operator to set the dwell time for collecting data on a target ion when an SIM, MRM or similar type of measurement s performed.

Solution to Problem

The first aspect of the present invention developed for solving the previously described problem is a chromatograph mass spectrometer having a chromatograph for separating components in a sample and a mass spectrometer for performing a selective ion monitoring (SIM) measurement or a multiple reaction monitoring (MRM) measurement on the sample separated into the components by the chromatograph, with a plurality of kinds of ions as the targets to be monitored, the chromatograph mass spectrometer including:
  a) an event setter for allowing an analysis operator to set one or a plurality of kinds of ion species to be monitored in the SIM or MRM measurement, a measurement starting time and a measurement finishing time, as parameters for one event, as well as to set a plurality of events under the condition that measurement time ranges are allowed to overlap each other;

b) a loop-time target setter for allowing the analysis operator to set a target value of a loop time required for one cycle of SIM or MRM measurements sequentially performed for ion species set for one event or a plurality of events whose measurement time ranges are overlapped;

c) a dwell time calculator for calculating, for each event set by the event setter, a dwell time which is a data-collecting time per one ion species set in the event concerned, based on the target value of the loop time set by the loop-time target setter, the number of ion species to be monitored in the event concerned, and the number of events whose measurement time ranges overlap the measurement time range of the event concerned; and d) a result displayer for showing the value of the dwell time calculated by the dwell time calculator.

The second aspect of the present invention developed for solving the previously described problem is a chromatograph mass spectrometer having a chromatograph for separating components in a sample and a mass spectrometer for performing a selective ion monitoring (SIM) measurement or a multiple reaction monitoring (MRM) measurement on the sample separated into the components by the chromatograph, with a plurality of kinds of ions as the targets to be monitored, the chromatograph mass spectrometer including:

a) an event setter for allowing an analysis operator to set one or a plurality of kinds of ion species to be monitored in the SIM or MRM measurement, a measurement starting time and a measurement finishing time, as parameters for one event, as well as to set a plurality of events under the condition that measurement time ranges are allowed to overlap each other;

b) a loop-time target setter for allowing the analysis operator to set a target value of a loop time required for one cycle of SIM or MRM measurements sequentially performed for ion species set for one event or a plurality of events whose measurement time ranges are overlapped;

c) a dwell time calculator for calculating, for each event set by the event setter, a dwell time which is a data-collecting time per one ion species set in the event concerned, based on the target value of the loop time set by the loop-time target setter, the number of ion species to be monitored in the event concerned, and the number of events whose measurement time ranges overlap the measurement time range of the event concerned; and d) an analysis condition setter for setting, for each ion, the value of the dwell time calculated by the dwell time calculator as one of the analysis conditions for the SIM or MRM measurement of the ion concerned.

In the present invention, the chromatograph is a gas chromatograph or liquid chromatograph. The mass spectrometer is typically a quadrupole mass spectrometer or triple quadrupole mass spectrometer.

In the chromatograph mass spectrometer according to the present invention, before an analysis on a sample is performed, the analysis operator using the event setter sets the mass-to-charge ratios of the ions to be monitored in the SIM or MRM measurement (in the case of the MRM measurement, the mass-to-charge ratio of the precursor ion and that of the product ion), measurement starting time, measurement finishing time as well as other parameters for each event. The measurement time range, which is defined by the measurement starting time and the measurement finishing time, is determined according to the known retention time of each compound to be analyzed. Therefore, in order to enable the detection of a plurality of compounds having different retention times, the overlapping of the measurement time ranges of different events should be allowed.

On the other hand, the measurement of an ion originating from one specific compound is performed only intermittently at intervals of time determined by the loop time. Therefore, in order to correctly determine the shape of the peak on the chromatogram, the loop time should be limited so as not to exceed a certain value. Accordingly, the analysis operator specifies the target value of the loop time using the loop-time target setter. Even if the loop time is the same, the dwell time for one ion species in a certain range of time will be shortened if a greater number of ion species to be analyzed are assigned to that range of time. Therefore, for example, in response to a predetermined operation by the analysis operator, the dwell time calculator finds, for each event, the largest value of the number of events whose measurement time ranges overlap that of the event concerned, and calculates the dwell time based at least on the found number of events, the target value of the loop time and the number of ion species to be monitored in the event concerned. The greater the number of ion species set in the event is, the shorter the dwell time will be. Furthermore, under normal conditions, the dwell time will be shorter as the number of overlapping events becomes greater.

In the case of the quadrupole mass spectrometer, a certain amount of time is required to switch the voltage applied to the quadrupole mass filter when switching the kind of ion species to be analyzed, so that a pause time taking into account the switching time is provided for every switching of the target ion. Accordingly, this pause time should also be considered in calculating the dwell time.

In the chromatograph mass spectrometer according to the first aspect of the present invention, the result displayer shows the value of the dwell time calculated for each event by the dwell time calculator; for example, it shows the dwell time for each "partial measurement time range", which is a segment of time during which the state of the overlapping events (the kinds and number of events) does not change. Normally, if there are a plurality of events overlapping each other in a partial measurement time range, the dwell time varies from event to event. In that case, the dwell time is shown as a value with a certain breadth (i.e. a range defined by the largest and smallest values of the dwell time calculated for the plurality of events set in the partial measurement time range in question). The analysis operator visually checks the displayed value of the dwell time and determines whether or not that value is appropriate. For example, when the dwell time is considered to be too short, the analysis operator can adjust the dwell time by changing the target value of the loop time, or by changing the measurement starting time and/or measurement finishing time of one or more events so as to reduce the number of ion species to be simultaneously analyzed.

In the chromatograph mass spectrometer according to the second aspect of the present invention, the analysis condition setter sets, for each ion, the value of the dwell time calculated by the dwell time calculator, as one of the analysis conditions for the SIM or MRM measurement of the ion concerned. Since the dwell times obtained by calculations are thereby automatically reflected in the analysis conditions, the analysis operator does not need to manually input the values of the dwell. In the case where the dwell times automatically set as the analysis conditions are not directly used but need to be appropriately modified or corrected by manual operations, the automatic reflection of the calculated result facilitates the subsequent modifying task.

As a matter of course, the operation of reflecting the dwell times in the parameters of the analysis conditions by the analysis condition setter may be performed at the point in time when satisfactory dwell times are obtained by recalculation after the target value of the loop time and other parameters are corrected based on the result displayed by the result displayer in the previously described manner.

In the first aspect of the present invention, preferably, the result displayer may display the value of the dwell time for each partial measurement time range and additionally display, on the same view area, the smallest value of the dwell time among all of the partial measurement time ranges.

With this configuration, the analysis operator can quickly determine whether or not there is too short a dwell time, and efficiently determine whether or not the dwell times are appropriate.

More preferably, in the first aspect of the present invention, the result displayer may display, on the same view area, both the result of the dwell times and the largest value of the loop time computed based on the calculated dwell times among all of the partial measurement time ranges.

With this configuration, the analysis operator can quickly determine whether or not the actual loop time is shorter than the target value of the loop time.

In the first aspect of the present invention, an input-display field for the target value used in the loop-time target setter may preferably be provided on a view area on which the result of the calculation of the dwell time is displayed by the result displayer. Furthermore, an operation element (e.g. a GUI button) for commanding the dwell time calculator to perform calculations may also preferably be provided on the same view area. With this configuration, the sequential operation from the input of the target value of the loop time through the checking of the dwell time can be performed on a single view area.

Advantageous Effects of the Invention

With the chromatograph mass spectrometer according to the present invention, even when there is a large number of target compounds whose retention times are close to each other, the analysis operator only needs to input the target value of the loop time to obtain information about the dwell time of each event based on the events set at that point in time and other conditions. Therefore, the workload of the analysis operator in setting or correcting the dwell time or other related tasks will be reduced in both the case where the calculated dwell times are directly used as analysis conditions and the case where the analysis operator should correct or change the dwell times as needed. Consequently, the analysis task can be performed with a high level of efficiency as well as a low frequency of incorrect setting of the conditions due to an input error other causes.

Furthermore with the chromatograph mass spectrometer according to the present invention, the situation in which the data collection is performed under too short a dwell time can be avoided. Therefore, even for a compound with a comparatively low level of content, a sufficiently high peak can be located and a high level of quantitative accuracy can be achieved.

BRIEF DESCRIPTION OF DRAWINGS

FIG. 7 shows one example of the method-editing window in a conventional LC/MS/MS.

FIG. 8 shows one example of the loop-time listing window in a conventional LC/MS/MS.

DESCRIPTION OF EMBODIMENTS

A liquid chromatograph triple quadrupole mass spectrometer (which is hereinafter called the "LC/MS/MS") as one embodiment of the present invention is hereinafter described with reference to the attached drawings.

Figure 1:
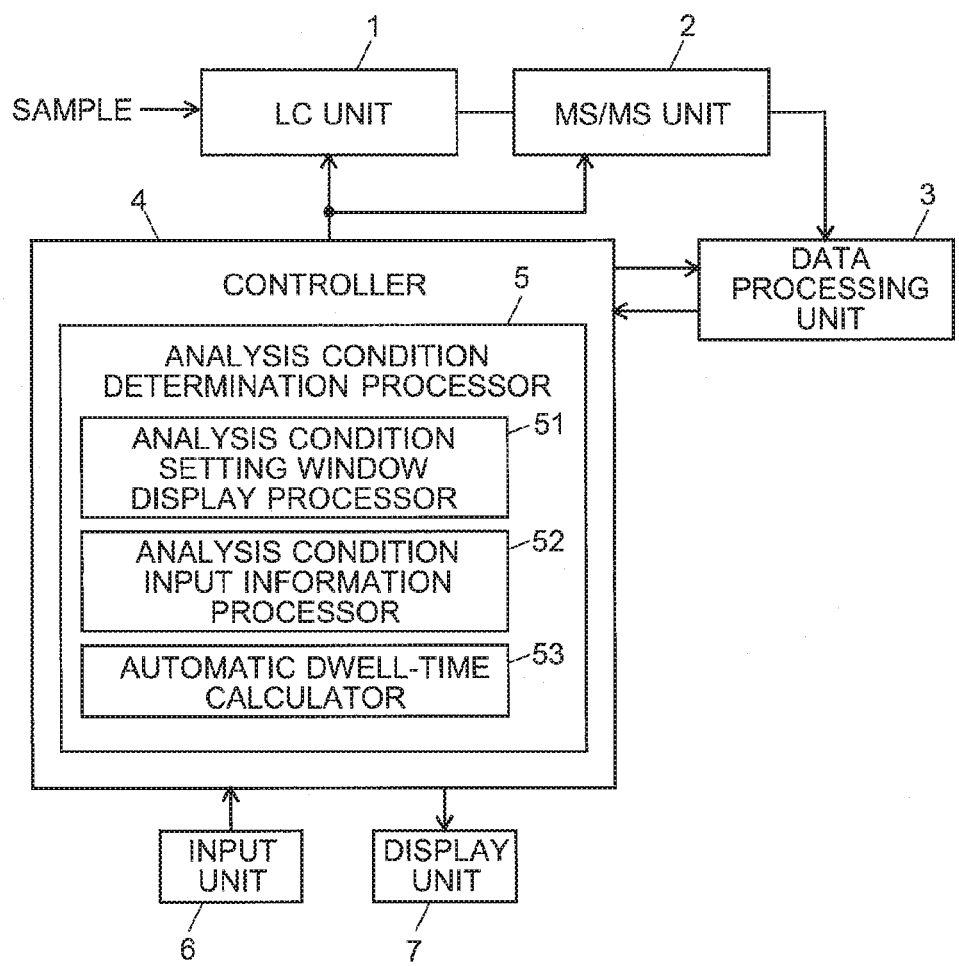
FIG. 1 is a configuration diagram of the main components of an LC/MS/MS as one embodiment of the chromatograph mass spectrometer according to the present invention.

FIG. 1 is a configuration diagram of the main components of the LC/MS/MS according to the present embodiment. The LC/MS/MS of the present embodiment includes a liquid chromatograph (LC) unit 1 for temporally separating various compounds contained in a sample and a triple quadrupole mass spectrometer (MS/MS) unit 2 for performing a mass spectrometry of the various compounds which have been separated.

Though not shown, the LC unit 1 includes a mobile-phase container holding a mobile phase, a liquid-sending pump for drawing the mobile phase and sending it at a fixed flow rate, an injector for injecting a sample into the mobile phase at a predetermined timing, a column for temporally separating various compounds in the sample, as well as other devices. On the other hand, the MS/MS unit 2 includes an atmospheric pressure ion source for ionizing the components contained in a liquid sample exiting from the column, a front quadrupole mass filter for selecting an ion having a specific mass-to-charge ratio among the ions derived from the compounds, a collision cell for fragmenting the selected ion (precursor ion) by a collision-induced dissociation process, a rear quadrupole mass filter for selecting an ion having a specific mass-to-charge ratio among the product ions produced by the fragmentation, a detector for detecting the selected product ion, and other devices.

The detection signals obtained with the MS/MS unit 2, i.e. the ion intensity signals originating from the components contained in the sample, are converted into digital values at predetermined intervals of sampling time by an A/D converter (not shown) and sent to a data processing unit 3. The data processing unit 3 performs predetermined computations on the obtained measurement data so as to create a mass spectrum or chromatogram as well as to perform a quantitative analysis. A control unit 4 controls the operations of the LC unit 1, MS/MS unit 2 and data processing unit 3.

The control unit 4 includes an analysis condition determination processor 5. The analysis condition determination processor 5 includes an analysis condition setting window display processor 51, an analysis condition input information processor 52, an automatic dwell-time calculator 53 and other functional blocks. The control unit 4 also has an input unit 6 and a display unit 7 connected to it. The input unit 6 consists of a keyboard and a pointing device (e.g. mouse) to be operated by analysis operators (users). The display unit 7 is used to display information entered and set by analysis operators as well as the results of analyses.

The data processing unit 3 and control unit 4 can be configured on a personal computer (including a CPU, memory and other components as hardware, with their functions realized by running, on this computer, a dedicated control and processing software program previously installed on the same computer.

In the LC/MS/MS of the present embodiment, various modes of analysis are available in the MS/MS unit 2; for example, the MRM measurement, precursor ion scan measurement, product ion scan measurement and neutral loss scan measurement are available for an analysis which involves fragmentation of ions, while the SIM measurement and scan measurement are available for an analysis which does not involve fragmentation of ions. In the LC/MS/MS of the present embodiment, before an analysis on a sample is performed, the analysis conditions including the aforementioned kind of analysis mode are set by the analysis operator, and subsequently, the analysis is automatically performed according to those analysis conditions. Hereinafter, the processes to be performed by the analysis condition determination processor 5 and other functional blocks in setting the analysis conditions, as well as the related tasks to be performed by analysis operators are described with reference to FIGS. 2-6.

Figure 2:
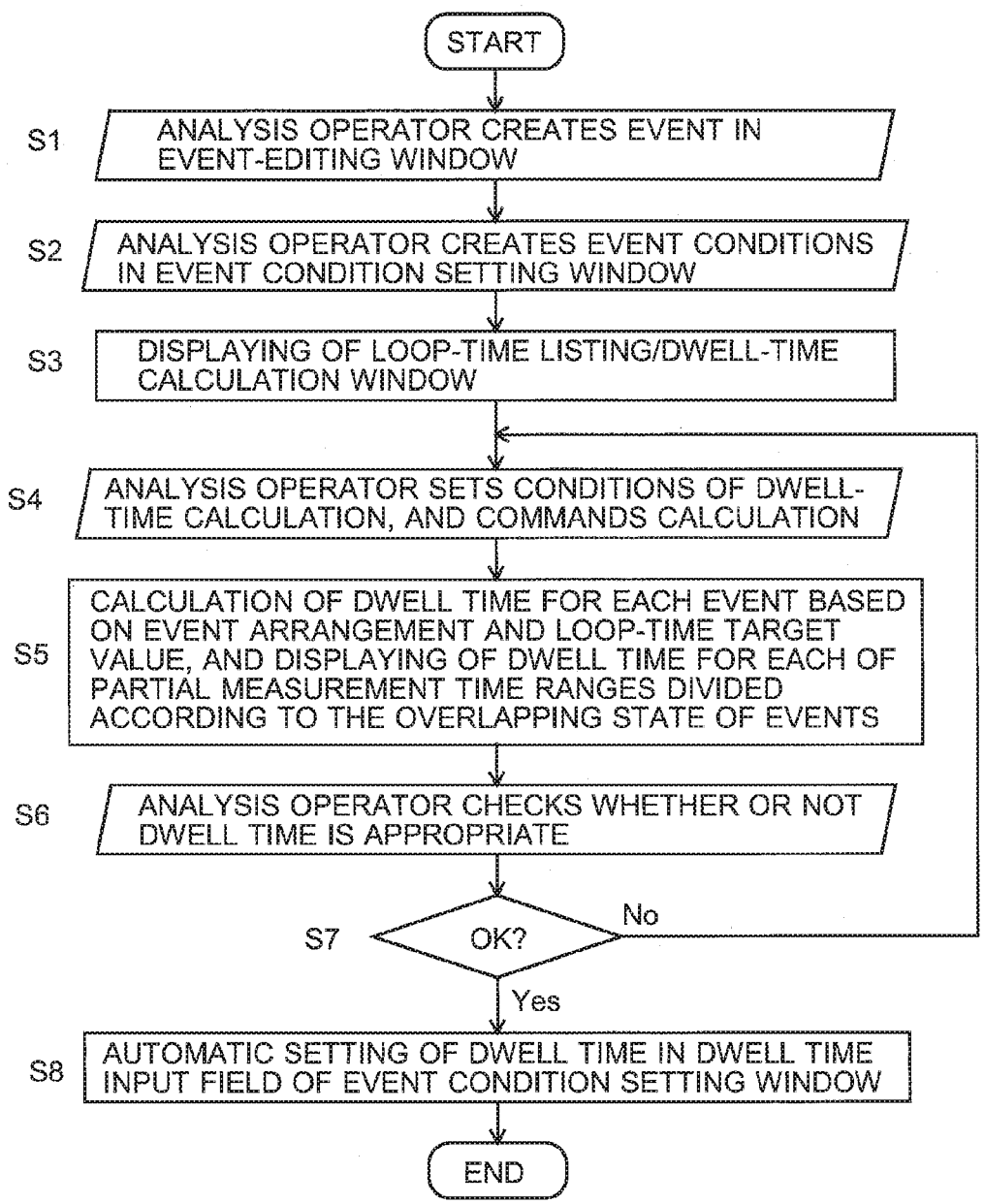
FIG. 2 is a flowchart of the tasks and processes performed in the process of setting the analysis conditions in the LC/MS/MS of the present embodiment.
Figure 3:
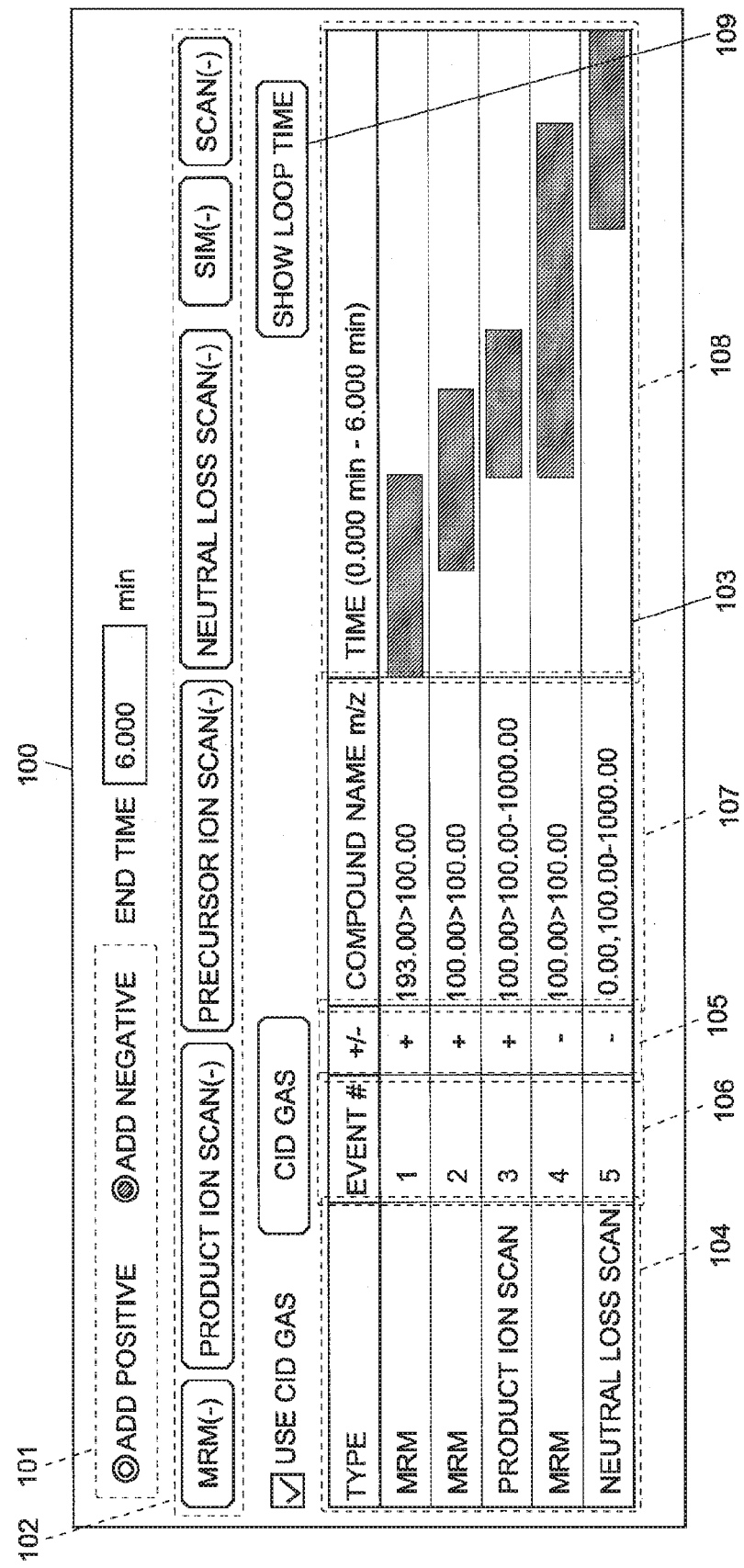
FIG. 3 shows one example of the event-editing window in the LC/MS/MS of the present embodiment.
Figure 4:
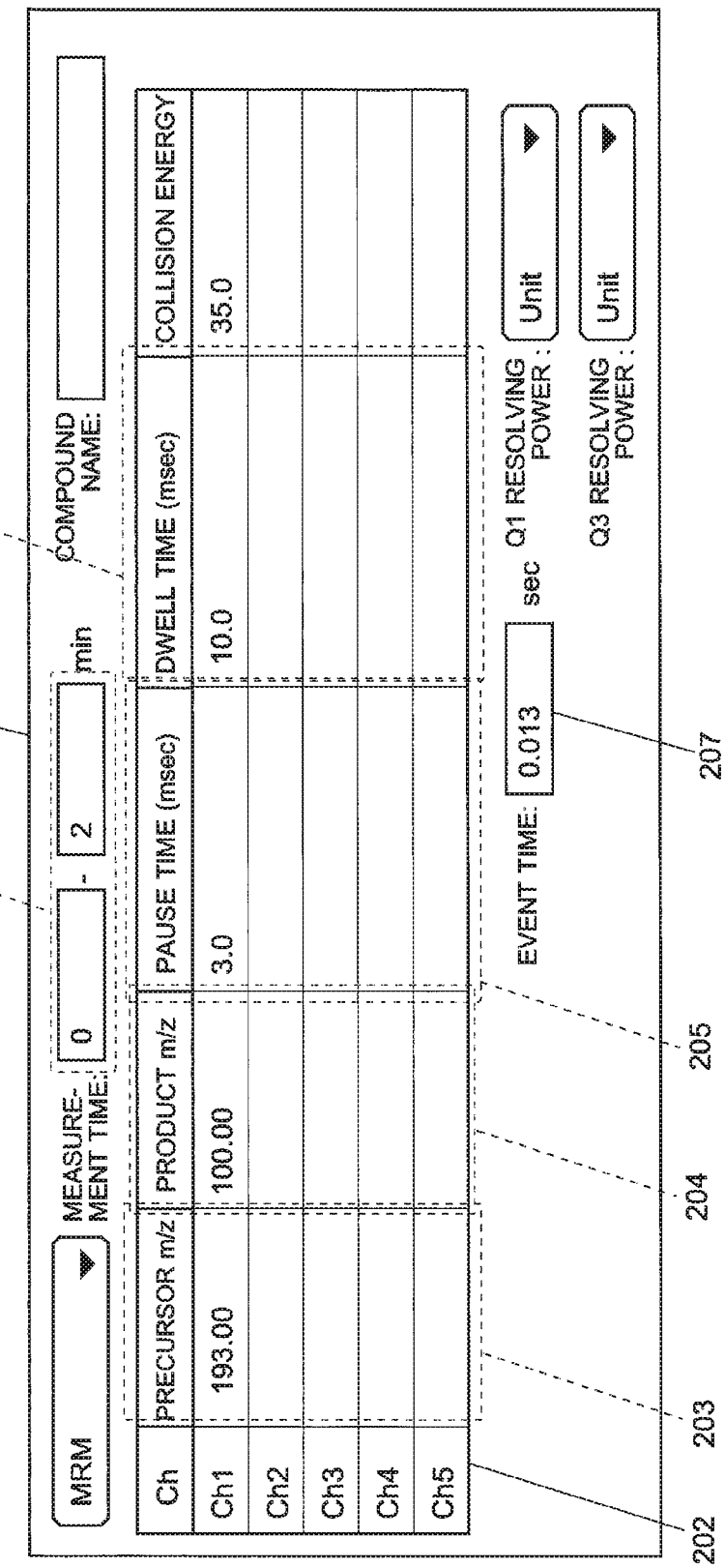
FIG. 4 shows one example of the SIM-measurement-type event condition setting window in the LC/MS/MS of the present embodiment.
Figure 5:
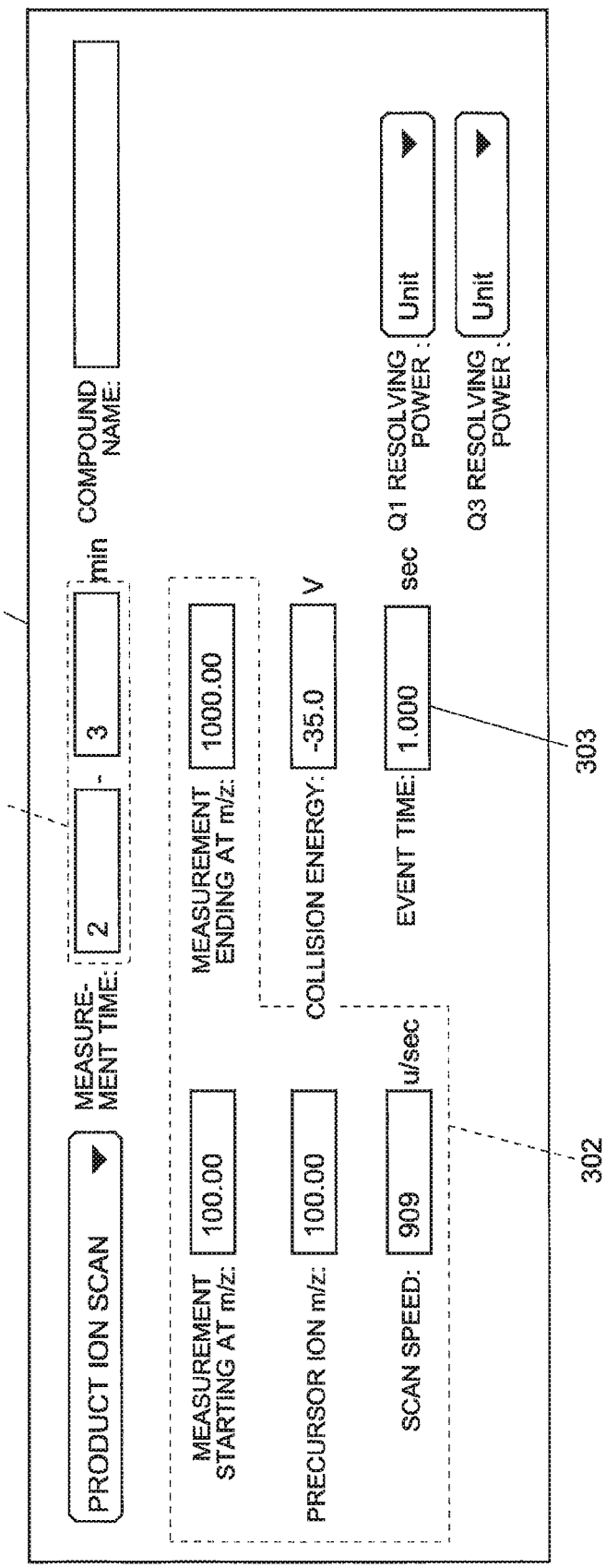
FIG. 5 shows one example of the scan-measurement-type event condition setting window in the LC/MS/MS of the present embodiment.
Figure 6:
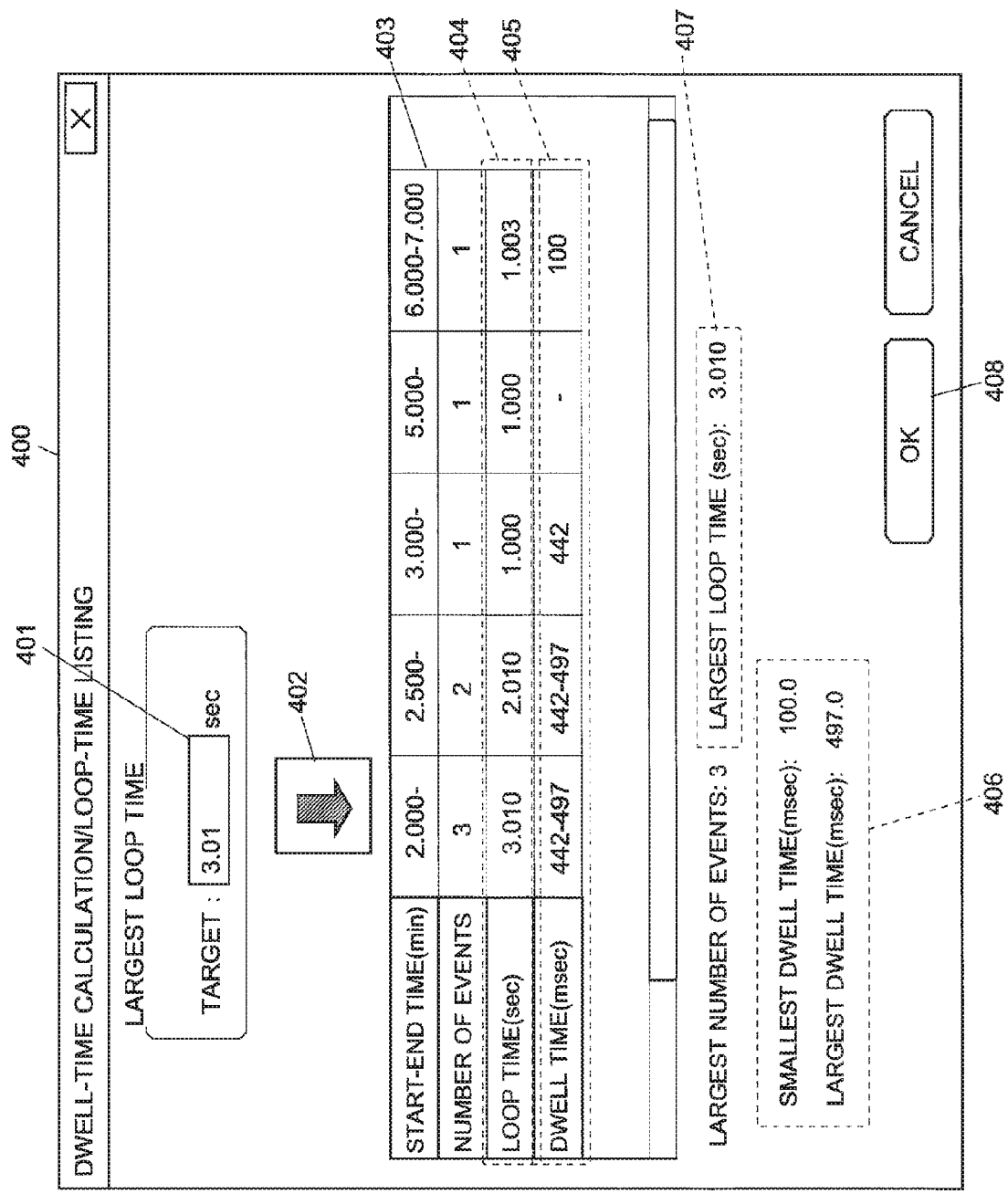
FIG. 6 shows one example of the dwell-time calculation/loop-time listing window in the LC/MS/MS of the present embodiment.
Figure 9A:
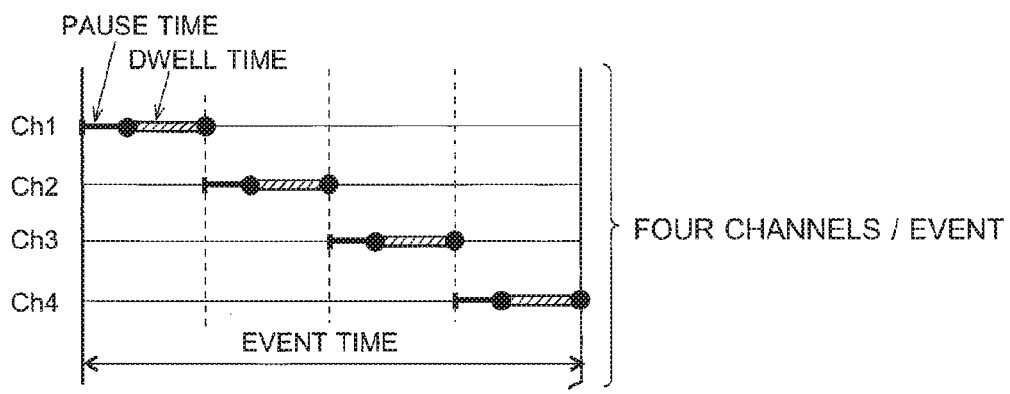
FIGS. 9A-9C are model diagrams showing the relationship between the event time and the loop time in the case where a plurality of events are temporally overlapped.
Figure 9B:
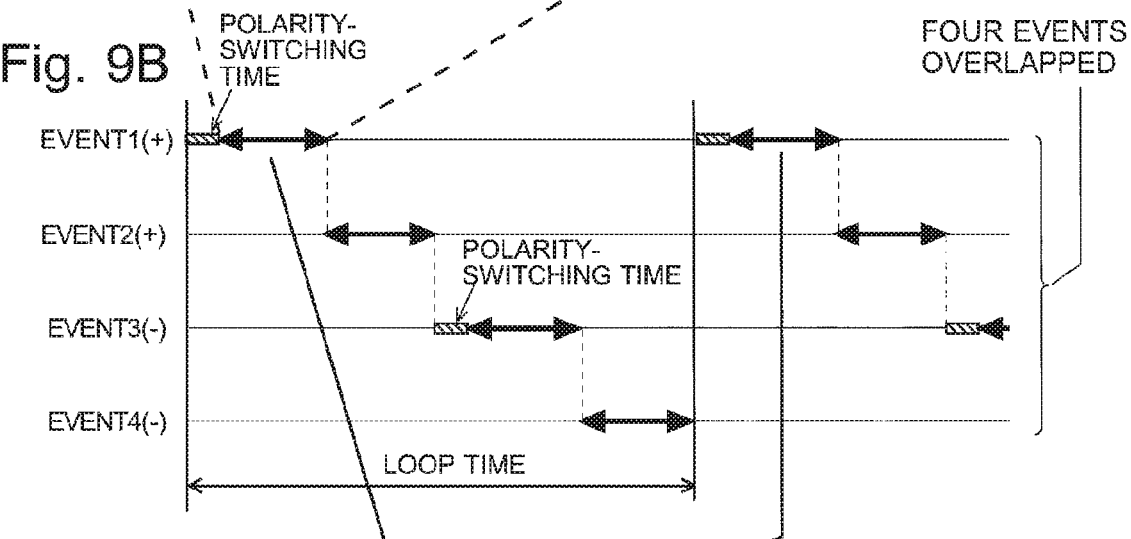
Figure 9C:
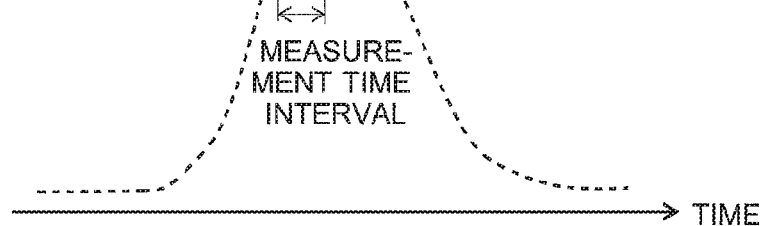

FIG. 2 is a flowchart of the tasks (operations) by analysis operators and the processes performed in setting the analysis conditions. FIG. 3 shows one example of the event-editing window used in setting the analysis conditions. FIG. 4 shows one example of the SIM-measurement-type event condition setting window used in setting the analysis conditions. FIG. 5 shows one example of the scan-measurement-type event condition setting window used in setting the analysis conditions. FIG. 6 shows one example of the dwell-time calculation/loop-time listing window used in setting the analysis conditions.

When the analysis operator performs a predetermined operation using the input unit 6, the analysis condition setting window display processor 51 responds to that operation and displays an event-editing window 100 as shown in FIG. 3 on the screen of the display unit 7. Although FIG. 3 shows some events already set, no event is actually set in the initial state of the window. On this event-editing window 100, the analysis operator creates events by the following procedure (Step S1).

Specifically, the analysis operator clicks one of the two radio buttons arranged in the polarity selection button area 101 to select the polarity of the ion to be analyzed in an event which is to be added. Subsequently, the analysis operator clicks one of the buttons arranged in the analysis mode addition button area 102 to select an analysis mode to be added (e.g. "MRM", "Precursor Scan", etc.). In response to these operations, the analysis condition input information processor 52 displays the specified analysis mode in the analysis mode display field 104 in the event information table 103. Thus, an event for performing the specified analysis mode is added. At this point, the polarity (+/−) selected by the operation on the radio buttons arranged in the polarity selection button area 101 is displayed in the polarity display field 105 in the event information table 103. Additionally, an "event number", which is a serial number indicating the order of addition, is automatically set in the event number display field 106. At the point when a new event is added in this manner, no information is displayed in the compound name m/z display field 107 and the measurement time display field 108.

Subsequently, the analysis operator sets detailed analysis conditions for the added event. For example, if the analysis mode of the added event is the SIM type, i.e. either an MRM or SIM measurement with no scan operation, when the analysis operator performs a predetermined operation using the input unit 6 (e.g. the clicking of a desired row in the event information table 103), the analysis condition setting window display processor 51 responds to this operation and displays an SIM-type event condition setting window 200 as shown in 4 on the screen of the display unit 7.

If the analysis mode of the added event is the scan type, i.e. any other mode than the MRM or SIM measurement, when the analysis operator performs a similar predetermined operation using the input unit 6, the analysis condition setting window display processor 51 responds to this operation and displays a scan-type event condition setting window 300 as shown in FIG. 5 on the screen of the display unit 7. The analysis operator sets the measurement time and other parameters of the added event on the SIM-type or scan-type event condition setting window 200 or 300 (Step S2).

For example, in the case of setting the analysis conditions for event number #1 for which the MRM measurement is selected as the analysis mode as shown in FIG. 3, the analysis operator enters the measurement starting time and measurement finishing time in the two text boxes arranged in the measurement time input area 201 on the SIM-type event condition setting window 200 as shown in FIG. 4. The system allows a simultaneous analysis of a plurality of ions having different mass-to-charge ratios in one event (although it is not strictly simultaneous but is performed in a time-shared manner with extremely short intervals of time), which can be set in the channel information table 202. In the example of FIG. 4, only one channel "Ch1" is set. The analysis operator inputs the mass-to-charge ratio values of the precursor ion and the product ion to be monitored in the MRM measurement in the precursor m/z display field 203 and the product m/z display field 204, respectively. In response to this input, the analysis condition input information processor 52 reflects the input information in the compound name m/z display field 107 in the event information table 103. The analysis operator also inputs the value of the pause time necessary for the switching of the mass-to-charge ratio in the pause-time display field 205.

In the conventional case, at this point, the analysis operator needs to additionally set the dwell time. The LC/MS/MS of the present embodiment does not require the manual setting of the dwell time. In FIG. 4, a numerical value is already displayed in the dwell time display field 206. When the SIM-type event condition setting window 200 has just been opened, an initial value is displayed in this field, and after a process (which will be described later) is performed, the display is automatically changed to the thereby obtained numerical value. Similarly, in FIG. 4, a numerical value (event time) is already displayed in the event-time input field 207. When the SIM-type event condition setting window 200 has just been opened, an initial value is displayed in this field, and after the event time is automatically calculated in the automatic dwell-time calculation process (which will be described later), the display is changed to the numerical value obtained by that calculation.

In the case of setting the analysis conditions for event number #3 for which, for example, the product ion scan is selected as the analysis mode as shown in FIG. 3, the analysis operator inputs the measurement starting time and measurement finishing time in the two text boxes arranged in the measurement time input area 301 on the scan-type event condition setting window 300 as shown in FIG. 5. The analysis operator also sets the beginning and ending mass-to-charge ratio values, scan speed and other parameters of the mass-to-charge ratio scan in the respective text boxes arranged in the scan information display area 302. Additionally, the analysis operator sets the event time of the added event in the event time input field 303.

Similarly to the conventional case, the measurement time range of each event, which is defined by the measurement starting time and measurement finishing time, needs to be set with attention to the following points:

(1) The measurement time range should be set with a certain amount of extra time before and after the retention time of the target compound.

(2) In the case where a plurality of events are set, the temporal overlapping of the events should basically be avoided as much as possible to achieve a high level of detection sensitivity. Needless to say, depending on the retention times of the target compounds, it may be difficult to completely eliminate the temporal overlapping of the events.

(3) For a compound which is previously known to be detectable with a high level of sensitivity (e.g. due to high concentration), the temporal overlapping of a plurality of events does not significantly affect its detection (in many cases, it practically causes no problem). Conversely, for a compound which is previously known to be detectable only a low level of sensitivity (e.g. due to low concentration), the temporal overlapping of the events should preferably be minimized.

The measurement time range (the measurement starting time and measurement finishing time set in the text boxes arranged in the measurement time input area 201 or 301 is reflected in the form of a band graph in the measurement time display field 108 in the event information table 103. As shown in FIG. 3, a glance at the graphs in this measurement time display field 108 provides a quick understanding of the state of overlapping or other aspects of the measurement time ranges among different events. While visually checking such a display, the analysis operator can adjust the measurement time range of each event taking into account the aforementioned points.

After the analysis conditions of each event have been set in the event condition setting window 200 or 300, the analysis operator clicks the loop time display button 109 arranged on the event-editing window 100. In response to this operation, the analysis condition setting window display processor 51 displays a dwell-time calculation/loop-time listing window 400 as shown in FIG. 6 on the display unit 7 (Step S3). On this dwell-time calculation/loop-time listing window 400, the analysis operator sets the target value of the loop time in the target loop time input field 401 as one condition of the automatic dwell-time calculation. Then, the analysis operator clicks the dwell time calculation button 402 to command the system to perform the automatic dwell-time calculation (Step S4).

Upon receiving this command, the automatic dwell-time calculator 53 calculates an optimum dwell time for the SIM-measurement-type event, based on the information set at that point in time, such as the information on the events set in the event information table 103 on the event-editing window 100 (mainly, their measurement time ranges), the detailed analysis conditions set on the event condition setting windows 200 and 300 (mainly, the number of channels and the pause time of each channel set in the channel information table 202), as well as the target value of the loop time entered in the target loop time input field 401 (Step S5).

That is to say, initially, based on the measurement time ranges of the events set in the measurement time display field 108 in the event information table 103, the automatic dwell-time calculator 53 examines the state of overlapping of the events and divides the entire measurement time range (from the starting time to the finishing time of the entire measurement) into a number of partial measurement time ranges during each of which the same state of overlapping of the events continues. Then, for each event, the calculator 53 determines the largest number of events overlapping in one or more partial measurement time ranges to which the event concerned belongs.

For example, in the case of event 1 in FIG. 3, there is a partial measurement time range overlapping with event 2, so that the largest number of SIM-type events overlapping each other is two. In the case of event 2, there is not only the partial measurement time range overlapping with event 1 but also another partial measurement time range overlapping with events 3 and 4. Event 3 is the scan-type event and should be excluded from the count, so that the largest number of SIM-type events overlapping each other is two. Using the largest number of overlapping events determined in this manner, the dwell time is calculated for each event from the target loop time entered the target loop time input field 401.

Specifically, the event time of each event is initially calculated by the following equation (1):

[event time]=([target loop time]−[polarity-switching time]×[number of cycles])/[largest number of overlapping events]    (1)

As noted earlier, there may be a plurality of channels set in one event, in which case the event time needs to be distributed to those Channels. In the present example, the time is equally distributed to the plurality of channels included in one event. Accordingly, the dwell time is calculated by dividing the event time by the number of channels and subtracting the pause time from the obtained value, as expressed by equation (2):

[dwell time]=([event time]/[number of channels])− [pause time]    (2)

By such calculations, the dwell time corresponding to the largest number of events overlapping the event concerned is determined for each event.

The calculated results are displayed in the loop time calculation result display field 404 and the dwell time calculation result display field 405 in the dwell-time/loop-time listing table 403 of the dwell-time calculation/loop-time listing window 400 for each of the divided partial measurement time ranges. As in the case of the partial measurement time range of 2.000-2.500 minutes in FIG. 6, if a plurality of events are assigned to one partial measurement time range, i.e. if there are a plurality of events overlapping each other, the dwell time is indicated as a value with a breadth defined by the largest and smallest values of the dwell time respectively calculated for the events assigned to the partial measurement time range concerned. For example, in FIG. 6, there are three events overlapping each other in the partial measurement time range of 2.000-2.500 min. The largest value of the dwell time calculated for those three events is 497 msec, and the smallest value is 442 msec. Accordingly, "442-497" is displayed in the dwell time calculation result display field 405.

Furthermore, below the dwell-time/loop-time listing table 403, the largest and smallest values among all dwell times are displayed in the largest/smallest dwell time display field 406, while the largest value among loop times is displayed in the largest loop time display field 407.

The analysis operator checks for any problems in the dwell times displayed in the dwell time calculation result display field 405. The analysis operator also Checks the range of the dwell time displayed in the largest/smallest dwell time display field 406 and determines whether or not the dwell time is too long, or conversely, too short (Steps S6 and S7). The loop time should also be checked. If there is a problem ("No" in Step S7), e.g. if the dwell time is too short, the process returns to Step S4, where the analysis operator appropriately changes the target value of the loop time set in the target loop time input field 401, and clicks the dwell time calculation button 402 to once more perform the automatic dwell-time calculation. Needless to say, it is also possible to return to the SIM-type event condition setting window 200 and change the measurement time before performing the automatic dwell-time calculation once again.

On the other hand, if there is no problem with the calculated dwell time or loop time ("Yes" in Step S7), the analysis operator clicks the OK button 408 in the dwell-time calculation/loop-time listing window 400. Then, the analysis condition input information processor 52 reflects the result of the dwell-time calculation at that point in time in the dwell time display field 206 in the channel information table 202 of each of the SIM-type events (Step S8). Consequently, the blanks in the channel information table 202 are filled and the analysis conditions are determined.

After the analysis conditions have been determined in this manner, the analysis operator enters an appropriate command using the input unit 6 to command the execution of the analysis according to the determined analysis conditions, whereupon the analysis is actually performed.

As shown in FIG. 3, a scan measurement, such as the product ion scan measurement, can also be set in the event instead of the SIM measurement. If an event in which a scan measurement is set ("scan-type event") is temporally overlapped, the event time entered in the event-time input field 303 for this scan-type event should be subtracted from the target value of the loop time entered in the target loop time input field 401 before the calculations expressed by equations (1) and (2) are performed. By excluding the scan-type events from the number of overlapping events in this manner, the dwell time can be correctly calculated.

In the case where the automatic dwell-time calculation process is performed, the same values of the dwell time and pause time are commonly applied to all channels set in one event. In the case where the automatic dwell-time calculation is not performed, the dwell time and pause time can be appropriately set for each channel.

It should be noted that the previously described embodiment is a mere example of the present invention, and any change, modification, addition or the like appropriately made within the spirit of the present invention will naturally fall within the scope of claims of the present application.

For example, it is evident that the present invention can also be applicable in a GC/MS/MS using a gas chromatograph instead of the liquid chromatograph, or in a LC/MS or GC/MS using a single-type quadrupole mass spectrometer instead of the triple quadrupole mass spectrometer. In the case of the LC/MS or GC/MS, the SIM-measurement type includes only the SIM measurement, since the MRM measurement cannot be performed by those types of apparatuses.

REFERENCE SIGNS LIST

1 . . . LC Unit
2 . . . MS/MS Unit
3 . . . Data Processing Unit
4 . . . Control Unit
5 . . . Analysis Condition Determination Processor
6 . . . Input Unit
7 . . . Display Unit
51 . . . Analysis Condition Setting Window Display Processor
52 . . . Analysis Condition Input Information Processor
53 . . . Automatic Dwell-Time Calculator
100 . . . Event-Editing Window
101 . . . Polarity Selection Button Area
102 . . . Analysis Mode Addition Button Area
103 . . . Event: information Table
104 . . . Analysis Mode Display Field
105 . . . Polarity Display Area
106 . . . Event Number Display Field
107 . . . Compound Name M/Z Display Field
108 . . . Measurement Time Display Field
109 . . . Loop Time Display Button
200 . . . SIM-Type Event Condition Setting Window
201, 301 . . . Measurement Time Input Area
202 . . . Channel Information Table
203 . . . Precursor m/z Display Field
204 . . . Product m/z Display Field
205 . . . Pause Time Display Field
206 . . . Dwell Time Display Field
207, 303 . . . Event Time Input Field
300 . . . Scan-Type Event Condition Setting Window
302 . . . Scan Information Display Area
400 . . . Dwell-Time Calculation Loop-Time Listing Window
401 . . . Target Loop Time Input Field
402 . . . Dwell Time Calculation Button
403 . . . Dwell-Time/Loop-Time Listing Table
404 . . . Loop Time Calculation Result Display Field
405 . . . Dwell Time Calculation Result Display Field
406 . . . Largest/Smallest Dwell Time Display Field
407 . . . Largest Loop Time Display Field
408 . . . OK Button

The invention claimed is:

1. A chromatograph mass spectrometer having a chromatograph for separating components in a sample and a mass spectrometer for performing a selective ion monitoring (SIM) measurement or a multiple reaction monitoring (MRM) measurement on the sample separated into the components by the chromatograph, with a plurality of kinds of ions as targets to be monitored, the chromatograph mass spectrometer including:

a) an event setter for allowing an analysis operator to set one or a plurality of kinds of ion species to be monitored in the SIM or MRM measurement, a measurement starting time and a measurement finishing time, as parameters for one event, as well as to set a plurality of events under a condition that measurement time ranges are allowed to overlap each other;

b) a loop-time target setter for allowing the analysis operator to set a target value of a loop time required for one cycle of SIM or MRM measurements sequentially performed for ion species set for one event or a plurality of events whose measurement time ranges are overlapped;

c) a dwell time calculator for calculating, for each event set by the event setter, a dwell time which is a data-collecting time per one ion species set in the event concerned, based on the target value of the loop time set by the loop-time target setter, a number of ion species to be monitored in the event concerned, and a number of events whose measurement time ranges overlap the measurement time range of the event concerned; and d) a result displayer for showing a value of the dwell time calculated by the dwell time calculator.

2. A chromatograph mass spectrometer having a chromatograph for separating components in a sample and a mass spectrometer for performing a selective ion monitoring (SIM) measurement or a multiple reaction monitoring (MRM) measurement on the sample separated into the components by the chromatograph, with a plurality of kinds of ions as targets to be monitored, the chromatograph mass spectrometer including:

a) an event setter for allowing an analysis operator to set one or a plurality of kinds of ion species to be monitored in the SIM or MRM measurement, a measurement starting time and a measurement finishing time, as parameters for one event, as well as to set a plurality of events under a condition that measurement time ranges are allowed to overlap each other;

b) a loop-time target setter for allowing the analysis operator to set a target value of a loop time required for one cycle of SIM or MRM measurements sequentially performed for ion species set for one event or a plurality of events whose measurement time ranges are overlapped;

c) a dwell time calculator for calculating, for each event set by the event setter, a dwell time which is a data-collecting time per one ion species set in the event concerned, based on the target value of the loop time set by the loop-time target setter, a number of ion species to be monitored in the event concerned, and a number of events whose measurement time ranges overlap the measurement time range of the event concerned; and d) an analysis condition setter for setting, for each ion, a value of the dwell time calculated by the dwell time calculator as one of analysis conditions for the SIM or MRM measurement of the ion concerned.

3. The chromatograph mass spectrometer according to claim 1, wherein:

the result displayer displays the value of the dwell time for each partial measurement time range and additionally displays, on a same view area, a smallest value of the dwell time among all of the partial measurement time ranges.

4. The chromatograph mass spectrometer according to claim 1 or 3, wherein:

the result displayer displays, on a same view area, both a result of the dwell times and a largest value of the loop time computed based on the calculated dwell times among all partial measurement time ranges.

5. The chromatograph mass spectrometer according to claim 1, wherein:

an input-display field for the target value used in the loop-time target setter is provided on a view area on which a result of the calculation of the dwell time is displayed by the result displayer.

6. The chromatograph mass spectrometer according to claim 3, wherein:

the result displayer displays, on a same view area, both a result of the dwell times and a largest value of the loop time computed based on the calculated dwell times among all partial measurement time ranges.

7. The chromatograph mass spectrometer according to claim 3, wherein:

an input-display field for the target value used in the loop-time target setter is provided on a view area on which a result of the calculation of the dwell time is displayed by the result displayer.

8. The chromatograph mass spectrometer according to claim 4 wherein:

an input-display field for the target value used in the loop-time target setter is provided on a view area on which a result of the calculation of the dwell time is displayed by the result displayer.

9. The chromatograph mass spectrometer according to claim 6 wherein:

an input-display field for the target value used in the loop-time target setter is provided on a view area on which a result of the calculation of the dwell time is displayed by the result displayer.

* * * * *